(12) United States Patent
Gruber

(10) Patent No.: US 9,320,919 B2
(45) Date of Patent: *Apr. 26, 2016

(54) SELECTIVE REMOVAL OF CELLS HAVING ACCUMULATED AGENTS

(71) Applicant: Siwa Corporation, Inc., Chicago, IL (US)

(72) Inventor: Lewis S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,081

(22) Filed: Apr. 7, 2014

(65) Prior Publication Data
US 2014/0303526 A1    Oct. 9, 2014

Related U.S. Application Data

(63) Continuation of application No. 12/951,768, filed on Nov. 22, 2010, now Pat. No. 8,721,571.

(51) Int. Cl.
*A61B 8/00* (2006.01)
*A61N 7/00* (2006.01)
*C12N 13/00* (2006.01)
*A61B 17/32* (2006.01)

(52) U.S. Cl.
CPC ... *A61N 7/00* (2013.01); *A61B 8/00* (2013.01); *A61B 17/320068* (2013.01); *C12N 13/00* (2013.01)

(58) Field of Classification Search
CPC ............. A61B 2019/52; A61B 17/225; A61B 19/5244; A61N 7/00
USPC .................. 600/437, 439; 601/1, 2
See application file for complete search history.

(56) References Cited

U.S. PATENT DOCUMENTS

| | | | |
|---|---|---|---|
| 4,217,344 A | 8/1980 | Vanlerberghe et al. | |
| 4,900,747 A | 2/1990 | Vlassara et al. | |
| 4,911,928 A | 3/1990 | Wallach | |
| 4,917,951 A | 4/1990 | Wallach | |
| 5,494,791 A | 2/1996 | Cohen | |
| 5,518,720 A | 5/1996 | Cohen | |
| 5,601,526 A | 2/1997 | Chapelon et al. | |
| 5,693,762 A | 12/1997 | Queen et al. | |
| 5,702,704 A | 12/1997 | Bucala | |
| 5,766,590 A | 6/1998 | Founds et al. | |
| 5,811,075 A | 9/1998 | Vlassara et al. | |
| 5,817,771 A | 10/1998 | Bayley et al. | |
| 5,984,882 A | 11/1999 | Rosenschein et al. | |
| 6,067,859 A | 5/2000 | Kas et al. | |
| 6,090,382 A | 7/2000 | Salfeld et al. | |
| 6,176,842 B1 | 1/2001 | Tachibana et al. | |
| 6,245,318 B1 | 6/2001 | Klibanov et al. | |
| 6,309,355 B1 | 10/2001 | Cain et al. | |
| 6,380,165 B1 | 4/2002 | Al-Abed et al. | |
| 6,387,373 B1 | 5/2002 | Wright et al. | |
| 6,670,136 B2 | 12/2003 | Schmidt et al. | |
| 6,676,963 B1 | 1/2004 | Lanza et al. | |
| 6,818,215 B2 | 11/2004 | Smith et al. | |
| 6,821,274 B2 | 11/2004 | McHale et al. | |
| 7,033,574 B1 | 4/2006 | Schneider et al. | |
| 7,101,838 B2 | 9/2006 | Stern et al. | |
| 7,256,273 B2 | 8/2007 | Basi et al. | |
| 7,347,855 B2 * | 3/2008 | Eshel et al. | 606/2.5 |
| 7,358,226 B2 | 4/2008 | Dayton et al. | |
| 7,367,988 B1 | 5/2008 | Litovitz | |
| 7,751,057 B2 | 7/2010 | Oldenburg et al. | |
| 7,815,570 B2 * | 10/2010 | Eshel et al. | 600/437 |
| 8,343,420 B2 | 1/2013 | Cioanta et al. | |
| 8,721,571 B2 | 5/2014 | Gruber | |
| 2002/0193784 A1 | 12/2002 | McHale et al. | |
| 2003/0073138 A1 | 4/2003 | Kientsch-Engel et al. | |
| 2003/0170173 A1 | 9/2003 | Klaveness et al. | |
| 2003/0229283 A1 | 12/2003 | Craig et al. | |
| 2004/0039416 A1 | 2/2004 | Myhr | |
| 2004/0141922 A1 | 7/2004 | Klaveness et al. | |
| 2004/0208826 A1 | 10/2004 | Schneider et al. | |
| 2004/0229830 A1 | 11/2004 | Tachibana et al. | |
| 2005/0084538 A1 | 4/2005 | Dayton et al. | |
| 2005/0283098 A1 | 12/2005 | Conston et al. | |
| 2006/0078501 A1 | 4/2006 | Goertz et al. | |
| 2006/0122543 A1 | 6/2006 | Mayer et al. | |
| 2006/0188883 A1 | 8/2006 | Murray et al. | |
| 2007/0059247 A1 | 3/2007 | Lindner et al. | |
| 2007/0065415 A1 | 3/2007 | Kleinsek et al. | |
| 2007/0083120 A1 | 4/2007 | Cain et al. | |
| 2007/0128117 A1 | 6/2007 | Bettinger et al. | |
| 2007/0129633 A1 | 6/2007 | Lee et al. | |
| 2008/0019986 A1 | 1/2008 | Stern et al. | |
| 2008/0051680 A1 | 2/2008 | Luebcke | |
| 2008/0063603 A1 | 3/2008 | Schneider et al. | |
| 2008/0139942 A1 | 6/2008 | Gaud et al. | |
| 2008/0160506 A1 | 7/2008 | Liu et al. | |
| 2009/0076390 A1 | 3/2009 | Lee et al. | |
| 2009/0306552 A1 | 12/2009 | Furuzono et al. | |
| 2010/0028359 A1 | 2/2010 | Gu et al. | |
| 2010/0226932 A1 | 9/2010 | Smith et al. | |
| 2011/0105961 A1 | 5/2011 | Gruber | |
| 2012/0130287 A1 | 5/2012 | Gruber | |
| 2012/0183534 A1 | 7/2012 | Gruber | |
| 2013/0243785 A1 | 9/2013 | Gruber | |

FOREIGN PATENT DOCUMENTS

| | | |
|---|---|---|
| AU | 2009248945 | 11/2012 |
| AU | 2009248945 | 4/2013 |

(Continued)

OTHER PUBLICATIONS

Wautier, J-L. et al., Protein Glycation: "A firm link to endothelial cell dysfunction", Circulation Research, Journal of the American Heart Association, vol. 95, pp. 233-238, (2004).

(Continued)

*Primary Examiner* — Joel Lamprecht
(74) *Attorney, Agent, or Firm* — Evan Law Group LLC

(57) ABSTRACT

A method of treating a condition associate with accumulation of an agent in cells in a patient includes exposing the cells to ultrasound, to selectively kill or induce apoptosis in the cells. The cells include the accumulated agent.

16 Claims, No Drawings

(56) References Cited

FOREIGN PATENT DOCUMENTS

| | | |
|---|---|---|
| AU | 2009248945 | 2/2014 |
| AU | 2009/248945 | 5/2014 |
| AU | 2011332143 | 6/2015 |
| AU | 2014202548 | 6/2015 |
| CA | 2724886 | 6/2014 |
| CA | 2724886 | 2/2015 |
| CN | 200980118817.6 | 5/2012 |
| CN | 200980118817.6 | 2/2013 |
| CN | 200980118817.6 | 10/2013 |
| CN | 200980118817.6 | 5/2014 |
| CN | 200980118817.6 | 10/2014 |
| CN | 200980118817.6 | 3/2015 |
| EP | 09 751 639.7 | 11/2011 |
| EP | 09 751 639.7 | 6/2012 |
| EP | 09 751 639.7 | 1/2013 |
| EP | 11776932.3 | 4/2013 |
| EP | 09751639.7 | 7/2013 |
| EP | 09751639.7 | 1/2014 |
| EP | 14170802.4 | 9/2014 |
| EP | 14170802.4 | 8/2015 |
| IL | 209513 | 8/2012 |
| IL | 209513 | 5/2013 |
| IL | 209513 | 5/2014 |
| IL | 209513 | 12/2014 |
| JP | 2011-511734 | 11/2013 |
| JP | 2011-511734 | 12/2014 |
| JP | 2015-076575 | 6/2015 |
| KR | 10-2012-7026063 | 7/2012 |
| KR | 10-2010-7026063 | 2/2013 |
| KR | 10-2010-7026063 | 9/2013 |
| KR | 10-2010-7026063 | 12/2013 |
| KR | 10-2013-7028228 | 6/2014 |
| KR | 10-2010-7026063 | 7/2014 |
| KR | 10-2012-7026483 | 7/2014 |
| KR | 10-2012-7026483 | 2/2015 |
| KR | 10-2013-7028228 | 4/2015 |
| KR | 10-2015-7007520 | 4/2015 |
| MX | 2010/012473 | 7/2013 |
| MX | 2010/012473 | 3/2014 |
| MX | 2010/012473 | 6/2014 |
| RU | 2010152693 | 12/2012 |
| RU | 2010152693 | 4/2013 |
| RU | 2010152693 | 5/2014 |
| RU | 2010152693 | 12/2014 |
| WO | 96/20958 | 7/1996 |
| WO | 97/49429 | 12/1997 |
| WO | 99/64463 | 12/1999 |
| WO | PCT/US2009/44951 | 7/2009 |
| WO | 2009/143411 | 11/2009 |
| WO | PCT/US2009/44951 | 12/2010 |
| WO | 2012/047629 | 4/2012 |
| WO | PCT/US2011/053399 | 4/2012 |
| WO | 2012/071269 | 5/2012 |
| WO | PCT/US12/31446 | 6/2012 |
| WO | PCT/US2011/061387 | 6/2012 |
| WO | 2012/135616 | 10/2012 |
| WO | PCT/US2011/061387 | 5/2013 |
| WO | PCT/US2012/031446 | 10/2013 |

OTHER PUBLICATIONS

International Search Report dated Jul. 21, 2009 for PCT application No. PCT/US2009/44951.

Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).

Ando, K. et al., "Membrane proteins of human erythrocytes are modified by advanced glycation end products during aging in the circulation", Biochemical and Biophysical Research Communications, vol. 258, pp. 123-127, (1999).

Jandeleit-Dahm, K. et al., "The AGE/RAGE axis in diabetes-accelerated atherosclerosis", Clinical and Experimental Pharmacology and Physiology, vol. 35, pp. 329-334, (2008).

Sakata, N. et al., "Immunohistochemical localization of different epitopes of advanced glycation end products in human atherosclerotic lesions", Atherosclerosis, vol. 141, pp. 61-75, (1998).

Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).

Aroian, R. et al., "Pore-forming toxins and cellular non-immune defenses (CNIDs)", Current Opinion in Microbiology, vol. 10, pp. 57-61, (2007).

Dobson, J., "A twist on tumour targeting", Nature Materials, vol. 9, pp. 95-96, (2010).

Gutensohn, K. et al., "Extracorporeal plateletpheresis induces the interaction of activated platelets with white blood cells", Vox Sanguinis, vol. 78, No. 2, pp. 101-105, (2000).

Horiuchi, S. et al., "Immunochemical approach to characterize advanced glycation end products of the maillard reaction", The Journal of Biological Chemistry, vol. 266, No. 12, pp. 7329-7332, (1991).

Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).

Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).

Carstensen, E.L. et al., "Lysis of erythrocytes by exposure to cw ultrasound", Ultrasound in Medicine and Biology, vol. 19, No. 2, pp. 147-165, (1993).

Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).

Iwata, H. et al., "Effect of carbonyl compounds on red blood cells deformability", Biochemical and Biophysical Research Communications vol. 321, pp. 700-706, (2004).

Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).

Self-Medlin, Y. et al., "Glucose promotes membrane cholesterol crystalline domain formation by lipid peroxidation", Biochimica et Biophysica Acta, vol. 1788, pp. 1398-1403, (2009).

Singh, N. et al., "The PPAR-y activator, rosiglitazone, inhibits actin polymerisation in monocytes: involvement of Akt and intracellular calcium", Biochemical and Biophysical Research Communications, vol. 333, pp. 455-462, (2005).

Li, Y-M. et al., "Effects of high glucose on mesenchymal stem cell proliferation and differentiation", Biochemical and Biophysical Research Communications, vol. 363, pp. 209-215, (2007).

Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).

Mi, Y. et al., "Apoptosis in leukemia cells is accompanied by alterations in the levels and localization of nucleolin", Journal of Biological Chemistry, vol. 278, pp. 8572-8579, (2003).

Christian, S. et al., "Nucleolin expressed at the cell surface is a marker of endothelial cells in angiogenic blood vessels", Journal of Cell Biology, vol. 163, No. 4, pp. 871-878, (2003).

Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).

Brundin, P. et al., "Prion-like transmission of protein aggregates in neurodegenerative diseases", Nature Reviews Molecular Cell Biology, vol. 11, No. 4, pp. 301-307, (2010).

Perez, C. et al., "Translational control of the abundance of cytoplasmic poly(A) binding protein in human cytomegalovirus-infected cells", Journal of Virology, vol. 85, No. 1, pp. 156-164, (2011).

Persson, J. et al., "Interleukin-lbeta and tumour necrosis factor-alpha impede neutral lipid turnover in macrophage-derived foam cells", BMC Immunology, vol. 9, No. 70, pp. 1-11, (2008).

Vergne, I. et al., "Cell biology of mycobacterium tubercolosis phagosome", Annu. Rev. Cell Dev. Biology, vol. 20, pp. 367-394, (2004).

(56) References Cited

OTHER PUBLICATIONS

Moskowitz, S.M. et al., "The role of pseudomonas lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arterioscerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-$1^{-/-}$ /low-density lipoprotein receptor$^{-/-}$ mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-y expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).

(56) References Cited

OTHER PUBLICATIONS

The Pink Book, Epidemiology and Prevention of vaccine preventable diseases, 11th Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11th Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).
Peters Jr. T.,"5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J. -L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).

Vlassara, H. et al, "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Vlassara, H. et al, "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erthrophagocytosis of human senescent erthrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS ONE, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
de Groot, K. et al., "Vascular endothelial damage and repair in antineutrophil cytoplasmic antibody—associated vasculitis", Arthristis & Rheumatism, vol. 56, No. 11, pp. 3847-3853, (2007).
Imani, F. et al., "Advanced glycosylation endproduct-specific receptors on human and rat t-lymphocytes mediate synthesis of interferon y: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS ONE, vol. 7, issue 1, pp. 1-11, (2012).

(56) References Cited

OTHER PUBLICATIONS

Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
U.S. Appl. No. 12/994,421, Jun. 14, 2012.
U.S. Appl. No. 12/951,768, Jul. 2, 2012.
U.S. Appl. No. 12/951,768, Mar. 30, 2012.
U.S. Appl. No. 12/994,421, Jul. 20, 2012.
U.S. Appl. No. 12/994,421, Sep. 10, 2012.
U.S. Appl. No. 12/951,768, Nov. 5, 2012.
U.S. Appl. No. 12/994,421, Feb. 26, 2013.
U.S. Appl. No. 12/951,768, Mar. 21, 2013.
U.S. Appl. No. 12/951,768, Mar. 27, 2013.
U.S. Appl. No. 12/994,421, May 21, 2013.
U.S. Appl. No. 12/994,421, Jul. 18, 2013.
U.S. Appl. No. 12/951,768, Jul. 29, 2013.
U.S. Appl. No. 12/951,768, Nov. 15, 2013.
U.S. Appl. No. 12/951,768, Dec. 20, 2013.
U.S. Appl. No. 12/994,421, filed May 22, 2009.
U.S. Appl. No. 13/332,976, filed Dec. 21, 2011.
U.S. Appl. No. 13/876,157, filed Sep. 27, 2011.
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα, Nα-Bis(carboxymethyl)-L-lysine trifluoroacetate salt≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in human proximal tubular cells", Clinical and Experimantal Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Leinenga, G. et al., "Scanning ultrasound removes amyloid-β and restores memory in an Alzheimer's disease mouse model", Science Translational Medicine, vol. 7, issue 278, pp. 1-11, (2015).

(56) References Cited

OTHER PUBLICATIONS

Shibayama, R. et al., "Autoantibody against N(epsilon)-(carboxymethyl)lysine: an advanced glycation end product of the Maillard reaction", Diabetes, vol. 49, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
Hargreaves, R.E.G. et al., "Selective depletion of activated T cells: the CD40L-specific antibody experience", TRENDS in Molecular Medicine, vol. 10, No. 3, pp. 130-135, (2004).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).
Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagai, R. et al., "Application of monoclonal antibody libraries for the measurement of glycation adducts", Biochemical Society Transactions, vol. 31, part 6, pp. 1438-1440, (2003).
U.S. Appl. No. 12/994,421, Mar. 13, 2015.
U.S. Appl. No. 13/332,976, Mar. 13, 2015.
U.S. Appl. No. 12/994,421, Mar. 27, 2015.
U.S. Appl. No. 13/332,976, Apr. 1, 2015.
U.S. Appl. No. 13/332,976, Sep. 3, 2014.
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
U.S. Appl. No. 13/332,976, Nov. 18, 2014.
U.S. Appl. No. 12/994,421, Nov. 18, 2014.
U.S. Appl. No. 13/332,976, Apr. 23, 2015.
U.S. Appl. No. 13/332,976, May 1, 2015.
U.S. Appl. No. 13/332,976, Jun. 11, 2015.

* cited by examiner

SELECTIVE REMOVAL OF CELLS HAVING ACCUMULATED AGENTS

CROSS REFERENCE TO RELATED APPLICATIONS

The present application is a continuation of U.S. application Ser. No.12/951,768 entitled SELECTIVE REMOVAL OF CELLS HAVING ACCUMULATED AGENTS, filed Nov. 22, 2010, now U.S. Pat. No. 8,721,571.

BACKGROUND

Accumulation of agents, such as proteins, lipids, bacteria, viruses, parasites or particles, leads to, or is associated with, pathological conditions. For example, nucleolin, a protein normally expressed in the nucleus or the cytoplasm has been shown to be expressed at the cell surface in neoplastic cells and endothelial cells of angiogenic vessels in vivo. Mi Y, et al. Apoptosis in leukemia cells is accompanied by alterations in the levels and localization of nucleolin. *J Biol Chem* 278: 8572-9 (2003); Sven C, et al. Nucleolin Expressed at the Cell Surface is a Marker of Endothelial Cells in Angiogenic Blood Vessels, *Journal of Cell Biology*, Vol. 164, No. 4, 871-878 (2003). Another example is P-glycoprotein (P-gp), a plasma membrane protein, which is over expressed in tumor cells that present a multidrug resistance (MDR) phenotype, which causes efflux of several structurally unrelated therapeutic drugs used for cancer treatment. Loo T W, et al. Identification of Residues in the Drug Translocation Pathway of the Human Multidrug Resistance P-glycoprotein by Arginine Mutagenesis, *Journal of Biological Chemistry*, Vol. 284, No. 36, 24074-24087 (2009). Deposition and subsequent accumulation of intracellular protein aggregates has been observed in several neurodegenerative disorders, such as α-synuclein in Parkinson's disease, β-amyloid and tau in Alzheimer's disease, and huntingtin in Huntington's diseases, and prion protein (PrP) in transmissible prion encephalopathies. Brandin P, et al. Prion-Like Transmission of Protein Aggregates in Neurodegenerative Diseases, *Nat Rev Mol Cell Biol.* Vol. 11, No. 4, 301-307 (2010). Poly A binding protein (PABP) accumulates in the cytoplasm of beta herpesviruses (HCMV)-infected cells. Perez C, et al. Translational control of cytoplasmic poly A binding protein (PABP) abundance in HCMV-infected cells, *J Virol.* Oct. 27 (2010) Epub.

Intracellular lipids accumulation is commonly observed in advanced atherosclerotic plaques. Monocyte infiltration in the intima layer of the vascular wall is followed by differentiation into macrophages, which in turn take up modified lipoproteins and become macrophage foam cells as a result of such intracellular lipids accumulation. Persson J, et al. Interleukin-1 beta and tumour necrosis factor-alpha impede neutral lipid turnover in macrophage-derived foam cells, *BMC Immunology*, 9(7) (2008). Obesity is associate with the accumulation of lipids in fat cells.

Some bacteria may accumulate inside cells, for example *Mycobacterium tuberculosis* and *Pseudomonas aeruginosa*. *M. tuberculosis* causes the formation of hard nodules or tubercles in the lungs, parasitizes macrophages by blocking the phagosome-lysosome fusion, a process called phagosome maturation arrest, and by replicating inside the phagosome. Vergne I, et al. Cell Biology of *Mycobacterium tuberculosis* Phagosome, *Ann Rev Cell Dev Biol.*, Vol. 20, 367-94 (2004). Similarly, P. aeruginosa colonizes the lungs of patients with cystic fibrosis and produces biofilms, alginates, and specific lipid A modifications, which allow the bacteria to escape immune response and cause severe chronic inflammation. Moskowitz S M, et al. The Role of *Pseudomonas* Lipopolysaccharide in Cystic Fibrosis Airway Infection, *Subcell Biochem.*, Vol. 53, 241-53 (2010). Production of biofilms by *Haemophilus influenzae, Streptococcus pneumoniae*, and other bacteria, has been linked to chronic otitis media in pediatric patients. Hall-Stoodley L, et al. Direct Detection of Bacterial Biofilms on the Middle-Ear Mucosa of Children With Chronic Otitis Media, *JAMA*, Vol. 256, No. 2, 202-11 (2006).

Some protozoan parasites present intracellular accumulation, for example *Plasmodium, Leishmania, Trypanosoma* and *Toxoplasma. Plasmodium*, the agent causing malaria, replicates and accumulates inside erythrocytes, provoking cell rupture and dissemination of the agent, while the main sites of sequestration of the infected erythrocytes containing the trophozoites, schizonts and gametocytes of the parasite have been shown to be the lung, spleen, and adipose tissue, but also the brain, skin, bone marrow, and skeletal and cardiac muscle. Franke-Fayard B, et al. Sequestration and Tissue Accumulation of Human Malaria Parasites: Can We Learn Anything from Rodent Models of Malaria?, *PLoS Pathogens*, Vol. 6, No. 9, e1001032 (2010). Similarly, *Leishmania mexicana* and *Trypanosoma cruzi* reside and proliferate inside macrophages. Zhang S et al. Delineation of Diverse Macrophage Activation Programs in Response to Intracellular Parasites and Cytokines, *PLoS Negl Trop Dis*, Vol. 4, No. 3: e648 (2010).

Viruses replicate in the host cell, and the accumulation of the viral particles may result in changes to the plasma membrane. Examples include HIV, hepatitis C and rhinovirus. Ma Y, et al. NS3 helicase domains involved in infectious intracellular hepatitis C virus particle assembly, J Virol. 82 (15) 7624-39 (2008); Korant B D, Butterworth B E, Inhibition by zinc of rhinovirus protein cleavage: interaction of zinc with capsid polypeptides, *J Virol.* 18(1):298-306 (1976).

Ultrasound is a technique that may be used to destroy or induce apoptosis of cells. U.S. Pat. No. 6,821,274 (2004). The technique has been used to selectively remove or kill cells based on differences is the membrane stiffness, such as that caused by cross-linking from AGE-modification. The ultrasound is targeted to harmonic frequencies of the cross-linked cell membranes or components. International Publication No. WO2009/143411 (2009).

SUMMARY

In a first aspect, the present invention is a method of treating a condition associate with accumulation of an agent in cells in a patient comprising exposing the cells to ultrasound, to selectively kill or induce apoptosis in the cells. The cells include the accumulated agent. The cells may be blood cells, such as red blood cells or white blood cells.

In a second aspect, the present invention is a method of removing cells from a sample, comprising exposing the sample to ultrasound, to selectively kill or induce apoptosis in the cells. The cells comprise an accumulated agent.

DETAILED DESCRIPTION

The present invention makes use of the discovery that the differential resonant frequency of a cell caused by the accumulation of at least one agent that causes, or is associated with, a pathological or undesired condition, such as proteins, lipids, bacteria, viruses, parasites or particles, may be used to distinguish and eliminate cells in which the accumulated agent leads to a difference in the resonant frequency of the cell, by applying ultrasound treatment. The cells associated with the accumulated agent have a resonant frequency which is distinct from cells of the same type. By selecting the frequency of the ultrasound applied to the tissue to feed energy into the resonant frequency, the cells with the accumulated agent will be destroyed or induced to undergo apoptosis. In an aspect of the invention, the cells are not AGE-modified cells. In another aspect of the invention, the cells are not tumor cells. In yet another aspect of the invention, the cells are not cancerous.

The ultrasound technique for removing cell-associated accumulation from a patient is selected for its ability to selectively kill or induce apoptosis in cells having accumulation of the agent associated with the pathological condition, while avoiding removal or destruction of cells that do not present the accumulation. For example, cells expressing high levels of nucleolin on the plasma membrane of the cell may be selected due changes in the stiffness and deformability of the cell. As used herein, "selectively kill or induce apoptosis" means that more of the cells which are the target of the killing or inducing apoptosis are so affected, as compared to other cell subject to the same exposure.

Ultrasound devices can be used according to practices well known to those skilled in the art to destroy cells by vibrational techniques, for example U.S. Pat. No. 5,601,526 (1997) and International Publication No. WO2009/143411 (2009). Ultrasound parameters, such as frequency, power and pulsation, can be screened for effectiveness in selectively destroying the targeted cells. Differential destruction or inducement of apoptosis may be by selection of the stiffer cells, or by selection of the cells by their resonant frequencies. Ultrasound as described above can be applied to a subject with monitoring to determine that inflammatory responses such as fever or swelling do not exceed limits well known to be safe. This process can be repeated at intervals to maintain a level of therapeutic benefit. Evaluation of improvement or maintenance of a desired result can be used to direct the frequency of reapplication of ultrasound according to the present invention. The application and reapplication can be determined with the goal of gradual improvement to avoid overwhelming natural mechanisms, such as removal of cells and cellular debris by scavenging cells.

A variety of techniques are available to determine whether ultrasound may be used to selectively remove or kill the cells having the accumulated agent, that leads to, or is associated with, a pathological or undesired condition. The stiffness of individual cells may be determined, by techniques such as those described in U.S. Pat. No. 6,067,859 (2000). Elastic properties of tissue may be measured, by techniques such as those described in U.S. Pat. No. 7,751,057 (2010). Furthermore, application of a variety of ultrasound parameters to cells or a tissue sample, followed by examination of the cells or the tissue sample for destruction or subsequent apoptosis, may also be used to determine whether ultrasound may selectively remove or kill the cells.

EXAMPLES

Example 1

(Prophetic) Ultrasound Removal of Cell-associated Accumulation of Nucleolin in Leukemia Cells Blood of a patient containing leukemia cells expressing nucleolin on the cell surface is treated with ultrasound. After first diagnosing the patient, a blood sample is taken for further analysis. Leukemia cells are isolated from the blood sample, and examined using an optical stretcher (U.S. Pat. No. 6,067, 859), to determine the relative stiffness of the cells and/or the resonant vibrational frequencies of the cell. This information is then used to select driving frequencies, intensity and length of time of treatment of the ultrasound, to selectively destroy or induce apoptosis, in the leukemia cells in vivo or ex vivo.

Example 2

(Prophetic) Ultrasound Removal of Cell-associated Accumulation of P-glycoprotein in Colon Cancer Cells Colon tissue from a patient containing colon cancer cells that present a multidrug resistance (MDR) phenotype are examined and determined to be overexpressing P-glycoprotein on the cell surface. The cells are then examined using an optical stretcher (U.S. Pat. No. 6,067,859), to determine the relative stiffness of the cells and/or the resonant vibrational frequencies of the cell. This information is then used to select driving frequencies, intensity and length of time of treatment of the ultrasound. For example, an ultrasound generating probe may be included at the tip of a colonoscopy device. The ultrasound generating probe could generate pulses of ultrasound at the appropriate frequency, to selectively destroy colon cancer cells that present a multidrug resistance (MDR) phenotype, after the probe has been placed proximate to the tumor. The success of the treatment is monitored by subsequent colonoscopy.

Example 3

(Prophetic) Ultrasound Removal of Cell-associated Accumulation of *Plasmodium*

Blood of a patient, containing erythrocytes infected with *Plasmodium*, is treated with ultrasound. After first diagnosing the patient, a blood sample is taken for further analysis. Erythrocytes infected with *Plasmodium* are isolated from the blood sample, and examined using an optical stretcher (U.S. Pat. No. 6,067,859), to determine the relative stiffness of the erythrocytes and/or the resonant vibrational frequencies of the erythrocytes. In addition, the *Plasmodium* parasite could also be examined using the optical stretcher, to determine ultrasound parameters capable of direct destruction of the parasite. This information is then used to select driving frequencies, intensity and length of time of treatment of the ultrasound, to selectively destroy infected erythrocytes and/or the *Plasmodium* parasites, in the patient's blood either in vivo or ex vivo.

Example 4

(Prophetic) Removal of Macrophages and Tubercles Infected with *Mycobacterium tuberculosis*

A biopsy of an area in the lung of a patient containing tubercles and macrophages infected with *M. tuberculosis* is taken. The biopsy is treated with ultrasound applied at a range of frequencies and intensities, to determine conditions necessary to selectively destroy or induce apoptosis in the infected marcophages, the tubercles and/or the *M. tuberculosis* bacterial cells. The lungs of the patient are then treated with ultrasound. Time of exposure may range from three to sixty minutes daily for up to 20 days. At the end of the treatment, the patients are tested to determine the reduction in the size and/or number of tubercles present in the lungs of the patient.

Example 5

(Prophetic) Removal of Alginates caused by *Pseudomonas aeruginosa* Infection in the Lungs of Patients with Cystic Fibrosis An alginate sample from the lungs of the patient is treated with ultrasound applied at a range of frequencies and intensities, to determine conditions necessary to selectively destroy or break down the alginate. The lungs of the patient are then treated with ultrasound. Time of exposure may range from three to sixty minutes daily for up to 20 days. At the end of the treatment, the patient is tested to determine the reduction of alginates in the lungs.

REFERENCES

1. Mi Y, et al. Apoptosis in leukemia cells is accompanied by alterations in the levels and localization of nucleolin. *J Biol Chem* 278:8572-9 (2003).
2. Sven C, et al, Nucleolin Expressed at the Cell Surface is a Marker of Endothelial Cells in Angiogenic Blood Vessels, *Journal of Cell Biology*, Vol. 164, No. 4, 871-878 (2003).
3. Loo T W, et al. Identification of Residues in the Drug Translocation Pathway of the Human Multidrug Resistance P-glycoprotein by Arginine Mutagenesis, *Journal of Biological Chemistry*, Vol. 284, No. 36, 24074-24087 (2009).
4. Brandin P, et al. Prion-Like Transmission of Protein Aggregates in Neurodegenerative Diseases, *Nat Rev Mol Cell Biol*. Vol. 11, No. 4, 301-307 (2010).
5. Perez C, et al. Translational control of cytoplasmic poly A binding protein (PABP) abundance in HCMV-infected cells, *J Virol*. October 27 (2010) Epub.
6. Persson J, et al. Interleukin-1 beta and tumour necrosis factor-alpha impede neutral lipid turnover in macrophage-derived foam cells, *BMC Immunology*, 9(7) (2008).
7. Vergne I, et al. Cell Biology of *Mycobacterium tuberculosis* Phagosome, *Ann Rev Cell Dev Biol*., Vol. 20, 367-94 (2004).
8. Moskowitz S M, et al. The Role of *Pseudomonas* Lipopolysaccharide in Cystic Fibrosis Airway Infection, *Subcell Biochem*., Vol. 53, 241-53 (2010).
9. Hall-Stoodley L, et al., Direct Detection of Bacterial Biofilms on the Middle-Ear Mucosa of Children With Chronic Otitis Media, *JAMA*, Vol. 256, No. 2, 202-11 (2006).
10. Franke-Fayard B, et al., Sequestration and Tissue Accumulation of Human Malaria Parasites: Can We Learn Anything from Rodent Models of Malaria?, *PLoS Pathogens*, Vol. 6, No. 9, e1001032 (2010).
11. Zhang S, et al. Delineation of Diverse Macrophage Activation Programs in Response to Intracellular Parasites and Cytokines, *PLoS Negl Trop Dis*, Vol. 4, No. 3: e648 (2010).
12. Ma Y, et al. NS3 helicase domains involved in infectious intracellular hepatitis C virus particle assembly, J Virol. 82 (15) 7624-39 (2008).
13. Korant B D, Butterworth B E, Inhibition by zinc of rhinovirus protein cleavage: interaction of zinc with capsid polypeptides, *J Virol*. 18(1):298-306 (1976).
14. U.S. Pat. No. 6,821,274 (2004).
15. International Publication No. WO2009/143411 (2009).
16. U.S. Pat. No. 5,601,526 (1997).
17. U.S. Pat. No. 6,067,859 (2000).
18. U.S. Pat. No. 7,751,057 (2010).

What is claimed is:

1. A method of treating a pathological condition associated with accumulation of an agent in cells in a patient, comprising:
   ascertaining a frequency and power sufficient to kill or induce apoptosis in the cells containing the accumulated agent, and
   exposing tissue containing the cells of the patient containing the accumulated agent and containing cells of the patient of the same type without the accumulated agent to ultrasound of the frequency and power sufficient to selectively kill or induce apoptosis in the cells containing the accumulated agent while sparing cells without the accumulated agent,
   wherein the cells containing the accumulated agent are not cancerous, and the agent is a protein.
2. The method of claim 1, wherein the cells containing the accumulated agent are not AGE-modified cells.
3. The method of claim 1, wherein the cells containing the accumulated agent are not tumor cells.
4. The method of claim 1, wherein the cells containing the accumulated agent are blood cells.
5. The method of claim 4, wherein the cells containing the accumulated agent are red blood cells.
6. The method of claim 4, wherein the cells containing the accumulated agent are white blood cells.
7. The method of claim 1, further comprising testing the cells, to determine ultrasound frequency and power to selectively kill or induce apoptosis in the cells.
8. The method of claim 7, wherein the testing comprises testing cells taken from the patient.
9. The method of claim 1, wherein exposing the cells comprises exposing the cells to a plurality of ultrasound treatments.
10. The method of claim 1, wherein the condition is a chronic disease.
11. The method of claim 1, wherein the protein is not an AGE-modified protein.
12. A method of removing a subset of cells from a tissue sample, comprising:
   ascertaining a frequency and power sufficient to kill or induce apoptosis in cells containing an accumulated agent,
   exposing the tissue sample to ultrasound of the frequency and power sufficient to selectively kill or induce apoptosis in the subset of cells while sparing cells without the accumulated agent,
   wherein the subset of cells contains the accumulated agent, and
   the tissue sample contains the subset of cells containing the accumulated agent and contains cells of the same type without the accumulated agent,
   wherein the cells containing the accumulated agent are not cancerous, and
   the agent is a protein.
13. The method of claim 12, wherein the sample is obtained from a patient.
14. The method of claim 12, wherein the cells containing the accumulated agent are not AGE-modified cells.
15. The method of claim 12, wherein the cells containing the accumulated agent are not tumor cells.
16. The method of claim 12, wherein the cells containing the accumulated agent are blood cells.

* * * * *